United States Patent
Kuznetsov et al.

(12) 
(10) Patent No.: US 6,444,204 B1
(45) Date of Patent: Sep. 3, 2002

(54) CANDIDA MALTOSA USED FOR THE BIO-DEGRADATION OF PETROLEUM PRODUCT POLLUTANTS

(76) Inventors: Petr Alexandrovich Kuznetsov, 350000, ul. Pervomaiskay, d.21, Krasnodar (RU); Penker Babaevna Avchieva, 117593, Litovsky bulvar, 3-2-543, Moscow (RU)

( * ) Notice: Subject to any disclaimer, the term of this patent is extended or adjusted under 35 U.S.C. 154(b) by 0 days.

(21) Appl. No.: 09/242,177
(22) PCT Filed: Feb. 2, 1998
(86) PCT No.: PCT/RU98/00029
§ 371 (c)(1), (2), (4) Date: Jun. 21, 1999
(87) PCT Pub. No.: WO98/55409
PCT Pub. Date: Dec. 10, 1998

(30) Foreign Application Priority Data
Jun. 5, 1997 (RU) ............................. 97109191

(51) Int. Cl.⁷ ............................. A01N 63/04; C12N 1/16
(52) U.S. Cl. ................. 424/93.51; 435/255.1; 435/255.4; 435/262.5
(58) Field of Search ............................. 435/255.1, 255.4, 435/262.5; 424/93.51

(56) References Cited

U.S. PATENT DOCUMENTS

| 3,870,599 A | * | 3/1975 | Azarowicz ............... 435/262.5 |
| 4,136,024 A | | 1/1979 | Bisa et al. |
| 5,494,580 A | | 2/1996 | Baskys et al. |

FOREIGN PATENT DOCUMENTS

| DD | 278355 | * | 5/1990 | ............... 435/262.5 |
| RU | 2007372 | | 2/1994 | |
| RU | 2014286 | | 6/1994 | |
| RU | 2023686 | | 11/1994 | |
| RU | 2076150 | | 3/1997 | |
| WO | WO95/31408 | | 5/1994 | |
| WO | WO95/06715 | | 7/1994 | |

OTHER PUBLICATIONS

E.I. Kvaonikov; T.M. Kiushnikova; Micro Organizmi Destructori Nefti V Vodnikh Basseinakh; 1981.

* cited by examiner

*Primary Examiner*—Irene Marx
(74) *Attorney, Agent, or Firm*—Knobbe, Martens, Olson & Bear, LLP

(57) ABSTRACT

The present invention relates to the field of bio-technologies and environmental protection, and refers the cleaning of water, soil and other media polluted with petroleum products. The cleaning method of the present invention is carried out with a biological preparation that comprises a pool of yeast of the *Candida maltosa* genus from the strains deposited under No. VKPM Y-2256 and No. VKPM Y-2257. These strains may be present in the pool in any ratio but preferably in the ratio of 1:1. The biological preparation may be used for removing pollution caused by a wide range of hydrocarbons contained in crude oil and petroleum products, for example fuel oil, oils, etc. The biological preparation affords recovery of oil pollution at temperatures up to +41° C. and pH 3.0–9.0, and may be used in saline ecosystems. The process for producing the biological preparation comprises simultaneously cultivating the above-mentioned yeast strains on a liquid medium followed by separation and removal of the biomass thus grown. To obtain a powdered preparation, the biomass is subjected to drying. When cleaning the above-cited media from oil pollution, an aqueous suspension of the biological preparation with a nitrogen-phosphate additive is used.

13 Claims, 1 Drawing Sheet

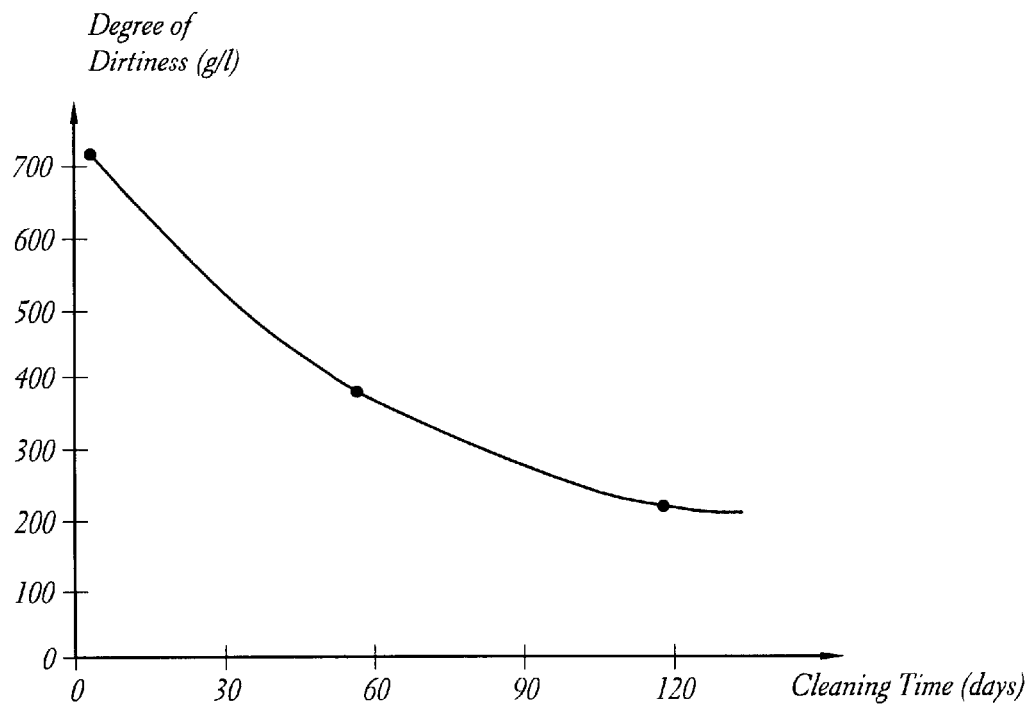
Fig. 1 CLEANING DYNAMICS OF THE SLUDGE SETTING TANK
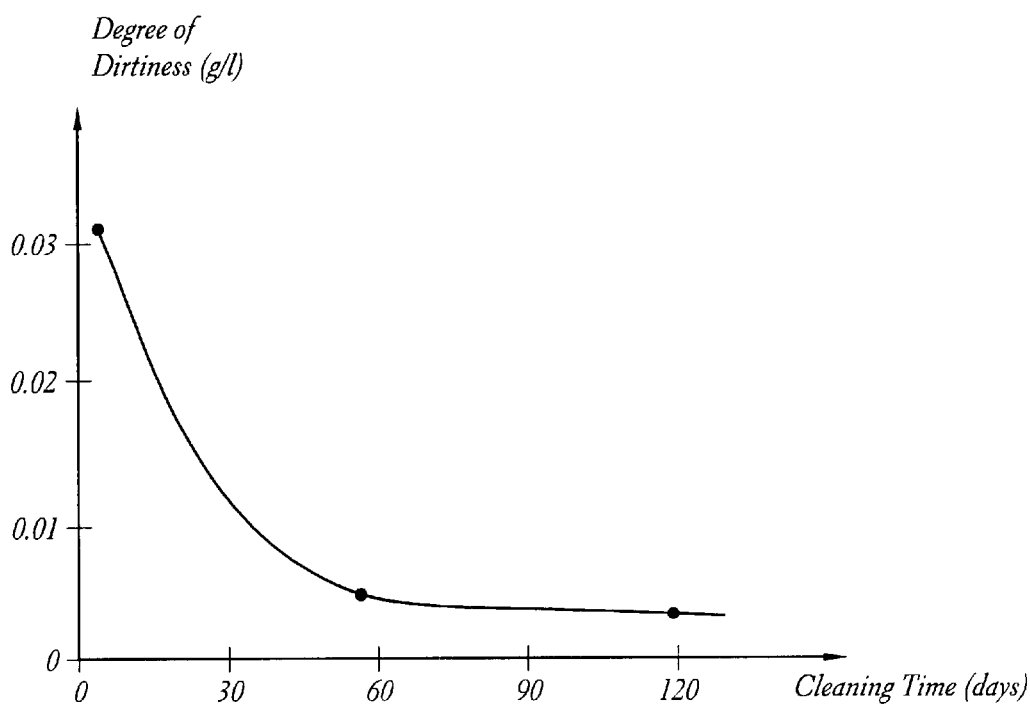
Fig. 2 CLEANING DYNAMICS OF THE WATER RESEVOIR

CANDIDA MALTOSA USED FOR THE BIO-DEGRADATION OF PETROLEUM PRODUCT POLLUTANTS

This application is the U.S. National Phase under 35 U.S.C. §371 of International Application PCT/RU98/00029, filed Feb. 2, 1998, which claims the benefit of priority under 35 U.S.C. §119 to Application No. RU 97109191/13, filed Jun. 5, 1997 in the Russian Federation.

FIELD OF THE INVENTION

The present invention relates generally to the field of bio-technologies and, more particularly, to microbiology and environmental protection, refers to the creation of a novel pool for cleaning oil-polluted soil, water and equipment, to the manufacture of a new biological preparation based on this pool designed to be used for the purification of water, industrial sewage, soil and other media from a wide range of petroleum products and directly from crude oil, and to the use of the obtained biological preparation for the efficient recovery of the above said oil-polluted media.

BACKGROUND OF THE INVENTION

The ever-growing volumes of oil output, transportation, refining and utilization result in the wide-spread pollution of water and soil areas with crude oil and oil products. Despite safety precautions taken, accidents intermittently occur at petroleum-extracting and oil-refining enterprises, pipelines, oil tankers, resulting in an environmentally hazardous oil and oil-product spillage. It is common knowledge that Nature itself possesses an efficient system for the recovery of oil-polluted areas by means of microorganisms capable of assimilating the hydrocarbons of oil. However, the microflora of Nature is no longer capable of effectively recovering million tons of oil finding every year its way into the environment. As a result, the mankind has found itself under the real threat of ecological disaster (see, L. R. Brown. *Chemical Engineering Progress*. (1987) Vol. 83, No. 10, pp. 35–40; "Oil-degrading microorganisms").

Such traditional methods of recovery as mechanical, chemical and physical fail to provide a sufficient degree of recovery of oil-polluted water and soil. Besides, in many cases the application of these methods inflicts a more pronounced damage on the environment than oil spillage itself.

In view of the above, biological methods of recovery of oil-polluted media recently find the ever-growing application, including the use of oil-oxidizing microorganisms. Analysis of the development of bio-technologies relating to the recovery of oil-polluted water and soil ecosystems and equipment enables one to come to the conclusion that the processes based on the oil-product biodegradation under the action of microorganisms are ecologically efficient. In accordance with known bio-technologies, the polluted medium may be exposed to the action of biological preparations, including microorganisms either in the form of pure isolated cultures or pools of microorganisms, that is to say a combination or association of two or more organisms. However, it should be emphasized that from the viewpoint of achieving of a more complete utilization of biotechnological functionality of microorganisms—oil biodegrading agents, the application of pure isolated cultures of microorganisms is less advantageous than that of mixtures or associations of microorganisms which, in virtue of their specificity, are capable of utilizing a wider range of compositionally heterogeneous substrates (industrial sewage, soil pollution, etc.) and provide degradation of organic compounds at the expense of a combined action of several types of microorganisms. Thus a more pronounced ecological efficiency of biotechnological decontamination and recovery is attained, said biotechnological decontamination and recovery being carried out for a shorter time.

As a rule, known biological preparations for the recovery of oil-polluted areas are characterized either by a relatively low efficiency in virtue of the selectivity of monospecies cultures used in the biological preparation or by complexity of producing the biological preparation, which is associated with the process for adapting microorganisms to the co-existence when using a microorganism pool in the biological preparation concerned.

Thus, there has been known the strain Phodococcus sp. HX7 possessing oil-oxidizing properties, which is used when cleaning water and soil from oil pollution. In the treatment of the polluted areas with this bacteria, the usual dose of application is 1 gram of the cellular biomass per square meter of a treated area; or in the case of using a suspension of the biological preparation based on the above-cited bacteria it contains $1·10^7$–$1·10^7$–$1·10^8$ cells in 1 milliliter ($1·10^7$–$1·10^8$ cells/ml). In so doing, the application rate of the suspension is 1 liter per square meter (1 l m$^2$) of an oil-polluted area.

However, the above-mentioned process for cleaning media from oil-pollution is insufficiently effective, since the use is made of a bacterial monospecies which limits a range of hydrocarbons to be purified. Besides, a process for growing such a culture is of long duration and may take as long as several days (see, Russian Patent No. 2,039,714, IPC C 02F 3/34, 1995).

Known in the prior art is the natural strain *Pseudomonas putida*-36 and its utilization for the recovery of oil-polluted soil (see, U.S. Pat. No. 4,822,490, IPC C 02F 3/34, 1989). In the known method of cleaning water and soil, a bacterial culture is applied to the oil-polluted area in the form of a biological preparation comprising the above-cited strain in admixture with a mineral fertilizer containing nitrogen in the nitrate form. The amount of the culture to be applied is at least $1·10^4$ cells/mg, where the flow rate of an aqueous mixture is from 0.5·to 1.0 liter per square meter.

However, the degree of recovery from various kinds of oil attained when using the above said bacterial strain also remains insufficient. Moreover, the application of this strain has certain limitations. This is associated with the fact that the strain grown on a standard carbohydrate substrate hardly adapts itself to new conditions, which means the necessity of using new substrates from soil. Besides, the said strain *Pseudomonas putida*-36 possesses hemolytic and gelatinizing activity which prevents the development of the process of natural self-recovery by means of microorganisms. Furthermore, the use of the nitrate forms of nitrogen when applying the bacterial culture into soil results in an additional contamination of the environment with toxic nitrate ions.

There has been known a pool of microorganisms Rhodococcus sp. Bkmac—1500D, Rhodococcus maris VKM AC-1501D, *Rhodococcus crythropolis* VKM AC-1502D, *Pseudomonas stutzeri* VKM B- 1972D, Candida sp. VKM-Y-2778D and a biological preparation produced using this pool for cleaning water and soil polluted with crude oil and oil products.

However, the known pool and biological preparation are insufficiently effective when cleaning oil-polluted media and, moreover, characterized by a complicated production method because of a great number of various microorganisms constituting the pool. The industrial employment of this biological preparation comprising the said pool is difficult for cleaning purposes, since five strains constituting the pool differ very much in their physiological features and have different growth characteristics.

A known process for producing a biological preparation based on this pool comprises preparation of a solution of a liquid nutrient medium containing the sources of nitrogen, phosphorus, trace elements and liquid paraffins as a carbon source, followed by cultivation, for example in a fermenter, of an inoculation medium in the form of the above-mentioned pool of microorganisms, at a temperature of 28° C. and pH maintained at 6.5–7.0. In so doing, the process of cultivation is carried out under aerobic conditions, for example when the medium is bubbled with the air flow. Thereafter, a biomass to be cultured is concentrated by the separation method and dehydrated by means of the lyophilic or thermal-vacuum drying to a 10% humidity. A biological preparation thus obtained contains $4 \cdot 10^{11} - 4 \cdot 10^{12}$ living cells per 1 gram and comprises both lipophilic and halophilic microorganisms. This biological preparation is capable of oxidizing petroleum products both in the zone of contacting with water and directly in an oil film and capable of removing oil pollution not only in the fresh but also in the saline ecosystem.

A known method of using the biological preparation obtained in accordance with the above described process consists in the utilization of an aqueous suspension prepared on its basis, in order to spray said suspension onto water and soil medium or the surface of equipment polluted with oil and/or oil-products. In so doing, a base suspension of the biological preparation is initially produced, said suspension being in the form of a concentrated aqueous solution of the biological preparation with a nitrogen-phosphate additive. To prepare this suspension, water having a temperature of from +15° C. to +30° C. is used. A composition thus prepared is maintained for 12 hours under stirring and aerating, after which time a base suspension is ready. To prepare a working suspension, the base suspension is supplemented with further nitrogen-phosphate additive followed by its dilution with water to obtain a desired concentration depending on the type of a medium to be cleaned and a degree of its pollution with oil and/or oil-products (see, Application PCT/RU 94/00103, IPC C 02F 3/34, 1995).

SUMMARY OF THE INVENTION

It is, therefore, an object of the present invention to provide a new pool of microorganisms and a biological preparation based thereof, which would possess improved properties: concurrent with the active work on the biodegradation of oil, in particular directly in an oil film, and of oil-processing products, would posses a shorter development cycle of microorganism components and would provide the biodegradation of a broad range of hydrocarbons constituting oil-processing products, under elevated temperatures and within a wide range of salinity of a medium to be recovered, and to provide most efficient methods for producing and utilizing this biological preparation.

A biological preparation in accordance with the present invention is a biodegrading agent for oil pollution. It includes a new pool comprising the yeast strains *Candida maltosa* VKPM Y-2256 and VKPM Y-2257. The strains *Candida maltosa* VKPM Y-2256 and VKPM Y-2257 have been selected from analogs isolated from oil-impregnated soil.

The two *C. maltosa* yeast strains VKPM Y-2256 and VKPM Y-2257 were deposited with the All Russia Collection of Industrially Deployed Microorganisms (State Scientific Research Institute of Genetics, $1^{st}$ Dorozhniy Proyezd, 1, GNII Genetika—VKPM, 113545 Moscow, Russia) on Mar. 3, 1997 under the registration numbers Y-2256 and Y-2257. They possess the following morphological-and-culture and physiological-and-biochemical properties.

The Strain *Candida maltosa* VKPM Y-2256

Morphological-and-culture Properties

On wort agar: the cells are oval and short-oval. Size of cells is 3.0–7.5×2.5–6.3 µm; fission is fast. In two-day culture in malt wort it forms islands of light dull film, a white dense sediment. Malt agar: large colonies, up to 0.7 cm in diameter, white color, shiny with yellowish shade in the middle part of the colony. A colony surface is smooth with an outlined pattern; a colony edge is fringed or even.

Physiological-and-biochemical Properties

In an oxygen-free habitat, it actively consumes glucose, Saccharose maltose, galactose, xylose; slightly worse—arabinose; does not assimilate lactose. Well assimilates the ammonium form of nitrogen; does not assimilate potassium nitrate. Grows at +5–+41° C. and pH 3.0–9.0. The growth optimum is at +30–+34° C. and pH 3.8–5.5.

The Strain *Candida maltosa* VKPM Y-2257

Morphological-and-culture Properties

The cells are oval and round-oval; single, as well as in the form of small chains (from three or four cells). Size of cells is 3.0–7.8×5.2–3.0 µm. Does not form ascospores. Medium—malt agar: colonies are round, smooth, cream-colored with a smooth surface and even edge. A colony center is elevated and slightly runs against the edge. In malt wort it forms a film; does not form rings. Sediment is dense, light.

Physiological-and-biochemical Properties

Aerobic properties. Well ferments glucose, saccharose, galactose, trehalose; slowly—maltose; does not ferment lactose and raffinose. Assimilates glucose, saccharose, maltose, galactose, xylose, trehalose, glycerol, adonitol, sorbitol, mannitol. Does not assimilate lactose, raffinose, ribose, erythritol, inositol, soluble starch. Well fixes the ammonium form of nitrogen. Does not fix potassium nitrate. Grows at +5—+41° C. and pH 3.0–9.0. The growth optimum is at +30–+41° C. and pH 3.5–5.5. The strains are stored at +18–+20° C. on wort agar.

BRIEF DESCRIPTION OF THE DRAWINGS

The various objects, advantages and novel features of the invention will be more readily apparent from the following detailed description when read in conjunction with the appended drawings, in which:

FIG. 1 shows the dynamics of cleaning a sludge setting tank in accordance with the present invention;

FIG. 2 shows the dynamics of cleaning a water area in accordance with the present invention.

BEST MODE TO CARRY OUT THE INVENTION

To prepare a new biological preparation, comprising a pool of the yeast strains *Candida maltosa* VKPM Y-2256 and *Candida maltosa* VKPM Y-2257, said strains are cultured by the continuous method (at the ratio of, e.g., 1:1) under conditions of aeration using natural or artificial hydrocarbon mixtures, for example oil distillates, at the ratio between isoparaffins and n-paraffins from 0.2:1 to 2:1, on an aqueous-mineral nutrient medium containing the sources of nitrogen, phosphorus, potassium and magnesium, at +30–+41° C. and pH 3.0–4.0; the medium dilution coefficient being $D=0.2$ hour$^{-1}$. The growth time is 5 hours. For the convenience of storage and transportation, the obtained yeast suspension is collected and thickened by decanting the aqueous phase, thereafter the biomass is separated and dried up to a humidity of no more than 12%. As can be seen from the foregoing, the process for producing a new biological preparation is rather simple.

Thus, for example to produce a new biological preparation, the yeast strains *Candida maltosa* VKPM Y-2256 and *Candida maltosa* VKPM Y-2257 are mixed. A qualitative relationship between individual strains may differ. However, taking into account the fact that growth parameters of the strains *Candida maltosa* VKPM Y-2256 and *Candida maltosa* VKPM Y-2257 are almost the same and their growth proceeds simultaneously in one vessel, preference is given to the ratio of said strains in the pool and the biological preparation based thereof to be 1:1. A mixture of the strains is cultivated, for example, in a fermenter, on a liquid nutrient medium constituting an aqueous solution which comprises the following mineral components in the composition, based on 1 liter of the obtained aqueous suspension:

| | |
|---|---|
| $H_3PO_4$ | 2.0–3.5 ml; |
| KCl | 0.8–1.5 g (or $K_2SO_4$— 1–2 g); |
| $MgSO_4$ | 0.5–1.0 g; |
| $FeSO_4.7H_2O$ | 0.1–0.2 g; |
| $ZnSO_4.7H_2O$ | 0.015–0.03 g; |
| $MnSO_4.7H_2O$ | 0.01–0.02 g; | a nitrogen-containing additive—allowing for the maintenance of nitrogen ranging from 300 to 800 mg per I liter of the obtained suspension.

Cultivation of the above said strains is carried out using a solution of the components referred to above at a temperature of +30–+41° C. The process of cultivation is performed under stirring and aerating while maintaining pH of the medium in a fermenter in the range of 3.0–4.0. Maintenance of the predetermined pH level is carried out by titrating the medium with alkali or acid depending on the initial pH level. In so doing, $NH_4OH$ and $H_2SO_4$ are preferably used as titrating alkali and acid, respectively. The process of cultivation may be carried out under both remove—fill-up and continuous conditions, with removing the biomass thus grown. The biomass removed from the fermenter is subjected to drying to a humidity of no more than 12% to ensure the content of living cells to be from $1 \cdot 10^6$ to $1 \cdot 10^8$ cells per 1 gram of dry biomass. The drying process is carried out with air preheated to +105–30 125° C.

The biological preparation thus obtained is a light yellow powder which possesses:

high oil-oxidizing activity, stability to chemical contamination, stability to sharp fluctuations of pH and temperature of the medium, ability to actively operate at temperatures from +5° C. to +41° C. and pH 3.0–9.0, adaptability to saline conditions of the medium (up to 15% NaCl), absence of toxicity and pathogenicity (as confirmed by the findings of the Research Institute of Labor Medicine of the Russian Academy of Medical Sciences).

It is also possible to produce and utilize the biological preparation in liquid form. In so doing, the biomass grown has to be supplemented with preservative and stabilizer components ensuring a long-term storage of the biological preparation prior to its use. The obtained biological preparation may operate both on an oil film surface and directly in the oil layer. It may be used for cleaning soil from oil pollution both by spraying and pumping down the subsoil layer. When oil penetrates into soil to a depth of up to 20 mm, the flow rate of the preparation is 0.2–0.3 g/m$^2$. As studies conducted at the Research Institute of Labor Medicine of the Russian Academy of Medical Sciences have shown, within 10 days, after application of the biological preparation to the polluted soil, the oil content has decreased by 30%, whereas when using thereof for cleaning a water surface, the oil film therein has been eliminated by 90%, which is confirmed by laboratory tests.

The present invention will become more apparent from the following non-limiting examples.

Example 1

To test the obtained biological preparation under an experimental procedure of the Research Institute of Labor Medicine of the Russian Academy of Medical Sciences, a foreign matter-free podzolic soil was used. The oil load was 40 g/kg. Trays (0.033 m$^2$; 10 cm high) were filled each with 8 kg of soil treated with a filtered-off household-fecal drainage water at the rate of 2 mg/kg. Four trays were used: No. 1—soil without oil and the biological preparation; No. 2—soil with the biological preparation but without oil; No. 3—soil with oil but without the biological preparation; No. 4—soil with oil and the biological preparation. Soil had been polluted with oil 5 days before the preparation was applied thereto. The preparation was applied to soil in the form of suspension. To this end, a base suspension was first prepared: a 100 ml vessel was filled with 1 g of the biological preparation obtained as a dry powder, 250 g of diammophos (a nitrogen-phosphate fertilizer) and 50 ml of warm water having a temperature of +15–+30° C. The above referenced ingredients were thoroughly mixed. Volume of the obtained suspension was then brought up to 100 ml by adding water thereto. A suspension thus obtained was then thoroughly mixed and aerated for 12 hours. Just before the soil treatment, the prepared base suspension was supplemented with further 3 g of diammophos, then diluted with water in the ratio of 1:100 and stirred. A working composition thus obtained was used to treat trays No. 2 and No. 4 filled with soil. Treatment was carried out with the working composition at the rate of 10 l per 1 m$^2$ of the surface (at room temperature). Observations were conducted for 20 days; then the oil content in soil was determined by the gravimetric method while extracting oil from soil with chloroform, followed by chromatographic separation. Sanitary and chemical indices: ammonium nitrogen, nitrites, nitrates, phosphates, permanganate oxidizability, dissolved oxygen, BOD, pH—were determined by conventional methods (see, Novikov, Yu. V. et al., "Methods for testing the water quality in water basins". Moscow, Medizdat, 1990). The results of studies on the oil degradation are summarized in Table 1 below. It can be seen from Table 1 that in the tray No. 3 filled with oil-polluted soil, the content of oil-processing products dissolved in chloroform has dropped for 10 days, at the expense of natural self-recovery processes, from 38.6 g/kg to 37.2. g/kg, that is to say, by 2.9%. In the tray No. 4, where oil-polluted soil was treated with the prepared composition, 10 days after treatment the content of oil extracted in chloroform has decreased from 40.8 g/kg to 28.2 g/kg, that is to say, by 30.8%. The ammonium nitrogen concentration in all four trays decreased by the $10^{th}$ day, but the maximum process intensity was recorded in the trays No. 2 and No. 4, that is to say, those treated with the claimed preparation. The process of nitrafication was observed within the same time limits. A maximal increase in the nitrate content also took place in the trays No. 2 and No. 4, where the claimed preparation was applied. As to the process of phosphorylation, it proceeded the most actively in the tray No. 4 (a phosphorus decrease against the background was 6.7%, whereas in the other trays this index varied from 22 to 49%). Treatment of oil-polluted soil with the claimed preparation had a beneficial effect on saprophyte microflora. Thus, the total microbe number (TMN) at +22 and +37° C. in soil of the tray No. 4 was higher than that in control (the tray No. 1), whereas in the tray where soil with oil was not exposed to the action of the claimed preparation, these indices were, throughout the entire experiment, by an order of magnitude lesser than that in the control tray No. 1. The absence of toxic action of the claimed preparation is confirmed by the results of the dehydrogenase test (cf., Table 1).

EXAMPLE 2

When evaluating the efficiency of water purification, 10-liter glass reservoirs filled with river water from Yauza River were used as experimental test models. Tests were carried out using four models: No. 1—river water without oil and the biological preparation; No. 2—river water with the biological preparation but without oil; No. 3—river water with oil but without the biological preparation; No. 4—river water with oil and the biological preparation. Water surface in each reservoir amounted to 201 cm². The load of oil-processing products onto water basins was created to be at the rate of 5 g/l. To evaluate an oil film degradation, "small" basins each with the capacity of 10 liters were used to accommodate 5 g of oil per 1 liter of river water. Treatment with the claimed preparation was carried out in two days following the application of oil to the test models. When treating models No. 2 and No. 4, a working composition was used. To prepare the working composition, a base suspension produced in accordance with Example 1 was diluted 10-fold. The working composition was applied at the rate of 1 l per 1 m² of the treated surface. The titer of microorganisms in the working composition amounted to $1 \cdot 10^8$ cells per gram. Observation of the water quality in the experimental models revealed high effectiveness of the pool when cleaning oil pollution. Thus, by the $10^{th}$ day, an oil film in the model No. 4 (water with oil and the preparation) has disappeared by 90% relative to the initial amount, whereas in the model No. 3 (water with oil but without the preparation) the amount of an oil film has decreased by no more than 10%. During the period under consideration, a level of the film oil-processing products dissolved in chloroform has decreased from 4.8 g to 1.7 g. Data of observations and analyses conducted are summarized in Table 2 below. The oil-processing product concentration in the aqueous layer dissolved in hexane has dropped in the model No. 4 from 7 mg/l to 5 mg/l. At the same time, in the model No. 3 (water with oil but without the preparation) the content of a film oil has dropped from 4.9 g to 4.5 g; in so doing, the oil content in the aqueous layer was found to be increased from 6 mg/l to 6.7 mg/l. Processes of nitrafication and phosphorylation become slower only in the model No. 3 where the decrease in oil pollution during the experimental period is insignificant. Decrease in permanganate oxidizability (PO) as well as in the content of dissolved oxygen (cf., Table 2) testifies to the occurrence of oil degradation processes under the action of the biological preparation applied. Low oxygen content in the water basins of models Nos. 2 and 4 and the level of BOD correlate with the amount of saprophyte microflora. Thus, data in Table 2 reflect a pronounced oil degradation in the presence of the claimed pool.

In much the same way as in Example 2 set forth above, experiments on cleaning the aqueous medium having an elevated salt content were conducted. Process parameters: a temperature of the medium to be cleaned is +32° C., pH 5.0. The initial amount of hydrocarbon content in the medium is 50 g/l. The results of the oil hydrocarbon biodegradation under the action of the claimed biological preparation in saline media are summarized in Table 3.

As experimental findings have shown, the pool in accordance with the present invention provides an efficient biodegradation of oil-polluted soil and water. Based on the data of hygienic examination carried out at the Research Institute of Labor Medicine of the Russian Academy of Medical Sciences, the pool in accordance with the present invention may be used unrestricted on a pilot and commercial scale.

TABLE 1

The results of experimental studies using soil models

| Date | Application time/days/ | Oil | No. 1 Without oil and Preparation | No. 2 Without oil, with preparation | No. 3 With oil, without preparation | No. 4 With oil and preparation |
|---|---|---|---|---|---|---|
| AMMONIUM NITROGEN (mg/l) | | | | | | |
| 10.11.96 | 5 | 1 | 34.7 | 339 | 14.4 | 800 |
| 20.11.96 | 15 | 10 | 12.2 | 19.65 | 6.21 | 58.5 |
| NITRITE NITROGEN (mg/l) | | | | | | |
| 10.11.96 | 5 | 1 | 1.58 | 1.65 | 0.69 | 1.6 |
| 20.11.96 | 15 | 10 | 0.88 | 0.98 | 0.58 | 0.3 |
| NITRATE NITROGEN (mg/l) | | | | | | |
| 10.11.96 | 5 | 1 | 0.4 | 0 | 0 | 0 |
| 20.11.96 | 15 | 10 | 6.5 | 209.6 | 2.76 | 198 |
| PHOSPHORUS (mg/l) | | | | | | |
| 10.11.96 | 5 | 1 | 0.75 | 1.92 | 0.92 | 4.32 |
| 20.11.96 | 15 | 10 | 0.38 | 1.32 | 0.72 | 1.4 |
| % drop | | | 49 | 31 | 21 | 67 |
| DROP IN CHLOROFORM-DISSOLVED OIL PRODUCTS (g/kg) | | | | | | |
| 10.11.96 | 5 | 1 | | | 38.6 | 40.8 |
| 20.11.96 | 15 | 10 | | | 37.2 | 28.2 |
| % drop | | | | | 2.9 | 30.8 |
| TOTAL MICROBE NUMBER (TMN) at 28° C. (cells/g) | | | | | | |
| 10.11.96 | 5 | 1 | $2.4 \cdot 10^5$ | $3.8 \cdot 10^6$ | $1.5 \cdot 10^4$ | $1.7 \cdot 10^4$ |
| 20.11.96 | 15 | 10 | $3.2 \cdot 10^5$ | $1.6 \cdot 10^6$ | $1.6 \cdot 10^4$ | $1.1 \cdot 10^4$ |
| TOTAL MICROBE NUMBER (TMN) at 37° C. (cells/g) | | | | | | |
| 10.11.96 | 5 | 1 | $3.4 \cdot 10^5$ | $2.5 \cdot 10^6$ | $1.5 \cdot 10^4$ | $2.3 \cdot 10^4$ |
| 20.11.96 | 15 | 10 | $4.0 \cdot 10^5$ | $1.4 \cdot 10^6$ | $1.6 \cdot 10^4$ | $8.9 \cdot 10^4$ |
| DEHYDROGENASE ACTIVITY Ent. coli, in min. (aqueous extract) | | | | | | |
| 10.11.96 | 5 | 1 | 48–58 | 54–60 | 98–106 | 100–109 |
| 20.11.96 | 15 | 10 | 54–66 | 56–62 | 100–11 | 64–68 |

TABLE 2

The results of experimental studies using water models

| | | | Models | | | |
|---|---|---|---|---|---|---|
| | | | No. 1 Control: water without oil and preparation | No. 2 Water with preparation without oil, | No. 3 Water with oil, without preparation | No. 4 Water with oil and preparation |
| Date | Application time/days/ Oil | Preparation | | | | |
| DISSOLVED OXYGEN (mg/l) | | | | | | |
| 15.11.96 | 3 | 1 | 7.6 | 2.9 | 3.2 | 1.4 |
| 20.11.96 | 8 | 5 | 7.4 | 1.4 | 3.4 | 0.98 |
| 25.11.96 | 13 | 10 | 7.4 | 0.98 | 3.2 | 1.2 |
| 30.11.96 | 18 | 15 | 7.2 | 1.6 | 4.6 | 2.3 |
| 02.12.96 | 21 | 18 | 7.4 | 2.7 | 4.8 | 4.1 |
| FIVE-DAY BIOCHEMICAL OXYGEN DEMAND (BOD, mg/l) | | | | | | |
| 25.11.96 | 13 | 10 | 1.8 | 10.3 | 2.1 | 11.1 |
| PERMANGANATE OXIDIZABILITY (PO, mg/l) | | | | | | |
| 15.11.96 | 3 | 1 | 14.2 | 14.8 | 20.2 | 22.1 |
| 20.11.96 | 8 | 5 | not found | not found | not found | not found |
| 25.11.96 | 13 | 10 | 12.6 | 14.0 | 18.6 | 10.6 |
| 30.11.96 | 18 | 15 | 11.2 | 13.1 | 12.4 | 11.0 |
| AMMONIUM NITROGEN (mg/l) | | | | | | |
| 15.11.96 | 3 | 1 | 0.22 | >8 | 0.26 | >8 |
| 20.11.96 | 8 | 5 | 0.02 | 3.4 | 0.04 | 3.8 |
| 25.11.96 | 13 | 10 | 0.1 | 3.0 | 0.08 | 1.0 |
| 30.11.96 | 18 | 15 | 0.04 | 2.0 | 0.04 | 0.6 |
| 02.12.96 | 21 | 18 | 0.001 | 0.8 | 0.001 | 0.4 |
| NITRITE NITROGEN (mg/l) | | | | | | |
| 15.11.96 | 3 | 1 | 0.004 | 0.06 | 0.004 | 0.06 |
| 20.11.96 | 8 | 5 | 0.15 | 0.1 | 0.06 | 0.01 |
| 25.11.96 | 13 | 10 | 0.003 | 0.004 | 0.001 | 0.04 |
| 30.11.96 | 18 | 15 | 0.004 | 0.004 | 0.003 | 0.1 |
| 02.12.96 | 21 | 18 | <0.001 | <0.001 | <0.001 | <0.001 |
| NITRATE NITROGEN (mg/l) | | | | | | |
| 30.11.96 | 18 | 15 | 0.4 | 0.38 | 0.6 | 0.4 |
| 02.12.96 | 21 | 18 | 0.8 | 4.0 | 0.98 | 6.8 |
| PHOSPHATES (mg/l) | | | | | | |
| 15.11.96 | 3 | 1 | 0.04 | 0.56 | 0.028 | 0.54 |
| 25.11.96 | 13 | 10 | 0.01 | 0.66 | 0.016 | 0.2 |
| pH VALUE | | | | | | |
| 15.11.96 | 3 | 1 | 7.7 | 7.5 | 7.3 | 7.5 |
| 25.11.96 | 13 | 10 | 7.8 | 7.7 | 7.4 | 7.4 |
| 30.11.96 | 18 | 15 | 7.8 | 7.4 | 7.4 | 7.7 |
| OIL-PRODUCT CONTENT IN FILM (small basins), g, (chloroform extract) | | | | | | |
| 15.11.96 | 3 | 1 | | | 4.9 | 4.8 |
| 25.11.96 | 13 | 10 | | | 4.5 | 1.7 |
| % drop | | | | | 3.2 | 61 |
| OIL-PRODUCT CONTENT IN AQUEOUS PHASE (mg/l) (dissolved in hexane) | | | | | | |
| 15.11.96 | 3 | 1 | | | 6.2 | 17.0 |
| 25.11.96 | 13 | 10 | | | 6.7 | 5.0 |
| % drop | | | | Increase | 8 | 29 |
| TOTAL MICROBE NUMBER (TMN) at 37° C. | | | | | | |
| 15.11.96 | 3 | 1 | $3.7 \cdot 10^2$ | $1.2 \cdot 10^2$ | $1.7 \cdot 10^2$ | $5.5 \cdot 10^2$ |
| 25.11.96 | 8 | 5 | $6.0 \cdot 10^2$ | 0 | $6.0 \cdot 10^2$ | $3.0 \cdot 10^2$ |
| DEHYDROGENASE ACTIVITY *Ent. coli*, in min. | | | | | | |
| 15.11.96 | 3 | 1 | 40–42 | 48–50 | 58–64 | 56–60 |
| 25.11.96 | 8 | 5 | 46–48 | 49–46 | 49–58 | 48–54 |

TABLE 3

Hydrocarbon biodegradation with the claimed pool at different degrees of the medium salinity

| NaCl concentration, g/l | Hydrocarbon concentration, % Duration of cultivation in days | | | | | |
|---|---|---|---|---|---|---|
| | 1 | 2 | 3 | 4 | 5 | 6 |
| 10.0 | 3.5 | 1.3 | 0.5 | 0.1 | — | — |
| 20.0 | 3.5 | 1.8 | 0.8 | 0.5 | 0.1 | 0.05 |
| 30.0 | 3.8 | 1.7 | 0.9 | 0.6 | 0.2 | 0.1 |
| 50.0 | 3.8 | 1.6 | 0.9 | 0.5 | 0.3 | 0.05 |
| 100.0 | 4.0 | 3.2 | 2.6 | 1.5 | 0.7 | 0.03 |
| 120.0 | 4.0 | 3.5 | 2.3 | 1.7 | 0.7 | 0.3 |
| 150.0 | 4.2 | 3.1 | 2.0 | 1.4 | 0.8 | 0.4 |

Industrial Applicability

The present invention may be used effectively on an industrial scale for the recovery of essentially any oil- and oil-product polluted soil and water ecosystems, including saline ones, and of the equipment of petroleum-extracting and oil-refining enterprises. The foregoing is confirmed by experiments conducted.

The biological preparation obtained in accordance with the present invention is used as follows.

A base suspension of the biological preparation is produced first. To this end, to 50 l of water having a temperature of +15–+30° C., a solution of 1 kg of the biological preparation and 0.25 kg of diammophos (or an equivalent amount of another nitrogen-phosphate additive) are added and thoroughly mixed. Volume of the obtained suspension is then brought up to 100 l by adding water thereto. A suspension thus obtained has to be aerated under stirring for 12 hours, thereafter it has to be supplemented with further 3 kg of diammophos (or an equivalent amount of another nitrogen-phosphate additive). As another nitrogen-phosphate additives, the use is possible of nitrogen-containing salts such as ammophos, sodium nitre, urea, ammonium chloride, an aqueous solution of ammonia, and phosphorus-containing salts such as phosphoric salts of alkali metals or fatty acids, for example palmitic acid or stearic acid. A mixture of diammonium phosphate (($NH_4$)$_2HPO_4$) and ammonium nitrate ($NH_4NO_3$) in the ratio of (0.5–1.5): (10–20), respectively, is the most preferable source of nitrogen and phosphorus. In the process of treating the polluted soil, water, equipment, a base suspension thus obtained is diluted with water in the ratio of 1:100, 1:10, 1:10, respectively. A working suspension obtained as a result of an intimate mixing is applied to the medium to be cleaned, preferably by the method of overhead irrigation.

To clean inner surfaces of the oil-polluted equipment (for example reservoirs), a working composition in the form of a 10-fold diluted base suspension of the preparation obtained in accordance with Example 1 is used. A reservoir to be cleaned is filled with the working composition to the level, or above the level of pollution of the reservoir walls. It is desirable that the process for cleaning be carried out in combination with other conventional means of cleaning certain reservoirs, for example in combination with mechanical cleaning. In the process of cleaning, it is necessary that the working composition be stirred and aerated, in order to promote the action of the claimed pool. In so doing, it is desirable to perform cleaning of the above-mentioned surfaces at pH 4.5–7.0 and temperatures ranging from +25° C. to +32° C.

EXAMPLE 3

Commercial tests run at the enterprise "Voronezhproduct" have shown that the use of a novel biological preparation provides a stable positive dynamics with respect to a degree of oil-product pollution of the medium to be cleaned. Tests were carried out in an oil-product polluted water basin having the total area of 2,000 m² and in a sludge setting tank having a polluted area of 1,500 m². The production of the base and working suspensions was carried out following the procedures reported in Examples 1 and 2. Prior to treatment, a degree of pollution of the media to be cleaned was determined. Depending on the type of the medium to be cleaned, the area of the polluted surface and the initial degree of pollution, the working suspension was applied in various amounts. Selection of the amount of the working suspension was carried out based on 1–3 kg of the biological preparation per 1 ton of pure oil. Throughout the tests, samples were taken; the results gained after their analysis are summarized in Table 4 and illustrated in the given diagrams. FIG. 1 shows the dynamics of cleaning a sludge setting tank in accordance with the present invention; FIG. 2 shows the dynamics of cleaning a water area in accordance with the present invention. Analysis of the samples was carried out by the chromatographic method.

TABLE 4

| Medium to be cleaned | Initial degree of pollution, g/l | Degree of pollution in g/l in accordance with the sample analysis | |
| --- | --- | --- | --- |
| Water area | 0.031 | 0.0056 | 0.004 |
| Sludge setting tank | 681.1 | 341.6 | 183.6 |

Note to Table 4. Test to determine the initial degree of the medium pollution was run on 02.07.97. Treatment of the polluted medium was carried out on the same day. Subsequent samplings were taken on 29.08.97 and 30.10.97, respectively.

Although the present invention has been described with reference to preferred embodiments, the invention is not limited to the details thereof, and various changes and modifications obvious to one skilled in the art to which the invention pertains are deemed to be within the spirit, scope and contemplation of the invention as further defined in the appended claims.

What is claimed is:

1. A mixture for removing oil in oil-polluted areas, said mixture comprising the isolated yeast strains *Candida maltosa* VKPM Y-2256 and *Candida maltosa* VKPM Y-2257.

2. A biological preparation for removing oil, comprising an active biocomponent and a nitrogen- and phosphorus-containing additive, wherein said biocomponent comprises a mixture of dried *Candida maltosa* VKPM Y-2256 and *Candida maltosa* VKPM Y-2257 and wherein the concentration of said biocomponent is from about $1 \times 10^6$ to $1 \times 10^8$ living cells per gram of dry biocomponent.

3. The biological preparation of claim 2, wherein the ratio of said strains is 1:1.

4. A method for producing a biological preparation for removing oil, comprising:

cultivating a mixture comprising *Candida maltosa* VKPM Y-2256 and *Candida maltosa* VKPM Y-2257 in a liquid nutrient medium, said liquid nutrient medium comprising a nitrogen- and phosphorus-containing additive, trace elements and liquid paraffin;

stirring and aerating the mixture to maintain a temperature of about 30° to 41° C. and a pH of about 3.0 to 4.0 thereby producing a biological preparation; and recovering the produced biological preparation.

5. The method of claim 4, wherein said cultivating is carried out continuously in a fermenter, such that any quantity of biological preparation which is recovered from the fermenter is replaced with a substantially equal quantity of nutrient liquid medium.

6. The method of claim 5, further comprising maintaining the pH of the nutrient medium by titrating said medium with alkali or acid, wherein $NH_4OH$ is used as said alkali and $H_2SO_4$ is used as said acid.

7. The method of claim 4, wherein said stirring and aerating of the medium are carried out by air bubbling.

8. The method of claim 4, further comprising:

drying said biological preparation to a humidity of no more than 12% with air preheated to 105°–125° C. until the concentration is from about $1 \times 10^6$ to $1 \times 10^8$ living cells per gram of dry biological preparation.

9. The method of claim 4, wherein the recovered biological preparation is supplemented with preservative and stabilizer components.

10. A method of removing oil from contaminated soil, water or equipment, comprising;

preparing an aqueous suspension by mixing the biological preparation of claim 2 with water at a temperature of 15° to 30° C. at a concentration of about 0.25 to 1.3 g of a nitrogen- and phosphorus-containing additive/100 g of water;

stirring and aerating said aqueous suspension for about 12 hours;

diluting the aerated aqueous suspension with water; and contacting said contaminated soil, water or equipment with the diluted aqueous suspension for a time under conditions sufficient to remove oil contamination.

11. The method of claim 10, wherein said nitrogen- and phosphate-containing additive comprises additives selected from the group consisting of a mixture of nitrogen-containing salts, an aqueous ammonia solution, phosphoric salts of alkali metals, and phosphoric salts of fatty acids, and wherein said nitrogen-containing salts are selected from the group consisting of diammonium phosphate, ammonium phosphate, sodium nitrate, a urea salt, and ammonium chloride.

12. The method of claim 10, for removing oil from contaminated soil, wherein said aqueous suspension is diluted with water in a ratio of about 1:50 to 1:100.

13. The method of claim 10, for removing oil from water or equipment, wherein said aqueous suspension is diluted with water in a ratio of about 1:5 to 1:10.

\* \* \* \* \*